United States Patent
Youn et al.

(10) Patent No.: US 6,610,715 B1
(45) Date of Patent: Aug. 26, 2003

(54) CATHECOL HYDRAZONE DERIVATIVES, PROCESS FOR PREPARING THE SAME AND PHARMACEUTICAL COMPOSITION CONTAINING THE SAME

(75) Inventors: Yong Sik Youn, Yongin-shi (KR); Myung Xik Xiang, Yongin-shi (KR); Byoung Chol Suh, Anyang-shi (KR); Jong Hoon Kim, Kwachun-shi (KR); Kwang Hyuk Lee, Kyungkee-do (KR); Eui Kyung Kim, Seoul (KR); Jae Kyu Shin, Anyang-shi (KR); Chung Keun Rhee, Seoul (KR)

(73) Assignee: Cheil Jedang Corporation, Seoul (KR)

( * ) Notice: Subject to any disclaimer, the term of this patent is extended or adjusted under 35 U.S.C. 154(b) by 0 days.

(21) Appl. No.: 09/959,947

(22) PCT Filed: May 28, 1999

(86) PCT No.: PCT/KR99/00264
§ 371 (c)(1),
(2), (4) Date: Nov. 13, 2001

(87) PCT Pub. No.: WO00/73280
PCT Pub. Date: Dec. 7, 2000

(51) Int. Cl.$^7$ .................... A61K 31/175; A61K 31/165; A61K 31/4409; C07C 281/14; C07D 213/81
(52) U.S. Cl. .................... 514/354; 514/530; 514/590; 514/614; 546/325; 560/27; 560/29; 564/151; 564/36; 564/250
(58) Field of Search .................... 546/325; 514/354, 514/530, 614, 590; 560/27, 29; 564/151, 36, 250

(56) References Cited

U.S. PATENT DOCUMENTS 3,753,680 A    8/1973   Tilles

FOREIGN PATENT DOCUMENTS

WO    WO 98/47869    10/1998

OTHER PUBLICATIONS

Prescott et al.; "Some New Thiosemicarbazones as Potential Chemotherapeutic Agents Indarolythiosemicarbazones" Int. Congr. Chemother., Proc., 5$^{th}$ 1967, 1(1), 23–33; Chem. Abstract, vol. 70, No. 21, May 26, 1969, pp. 339, the abstract No. 96701y.
Richard et al., "Oxidation of Aldehyde N,N–dialkyl–hydrazones with Hydrogen Peroxide . . . ", J. Org. Chem. 31(21), 4100–2 (1966), Chem. Abstract, vol. 66, No. 7, Feb. 13, 1967, pp. 2696, the abstract No. 28492y.

Prescoot et al., "Potential Antitumor Agents. Derivatives of 2–hydrazino–5–nitropyridine", J. Pharm. Sci. 1970, 59(1), 101–4, Chem. Abstract, vol. 72, No. 15, Apr. 13, 1970, pp. 225, 226, the abstract No. 77139w.
Kozlow et al., "Interaction of Schiffbases with Phenylhydrazine and its Nitro Derivatives", Tr. Prem. Sel.–Khoz. Inst. 1970, No. 68, 101–4 Chem. Abstract, vol. 77, No. 17,23.10.72, pp. 412, the abstract No. 113968e.
Chupakhin, "Reaction of Acridinium Salts with Phenylhydrazones and Phenylhydrazides," Khim. Geterotsikl. Soedin, 1975, (3), 387–91, Chem. Abstract, vol. 83, No. 3, Jul. 21, 1975, pp. 494, the abstract No. 28073p.
Kachroo et al., "Synthesis of Some Substituted–1,3,4–oxadiazoles, Their Antibacterial and Antiamebic Activity", Natl. Acad. Sci. Lett(India) 1991, 13(4), 125–6 Chemical Abstract vol. 115, No. 5, Aug. 5, 1991, pp. 832, the abstract No. 49539g.
Chen et al.: Acta Cystallogr. Sect. C, Cryst. Struct. Commun. 1997, C 53 (6), 775–77, vol. 127, No. 4, Jul. 28, 1997, p. 1388.

*Primary Examiner*—Joseph K. McKane
*Assistant Examiner*—Rebecca Anderson
(74) *Attorney, Agent, or Firm*—Birch, Stewart, Kolasch & Birch, LLP

(57) ABSTRACT

The present invention provides novel cathecol hydrazone derivatives of formula (I) or pharmaceutically acceptable salts thereof, wherein R$^1$ is C$_{1-7}$ alkyl or C$_{3-7}$ cycloalkyl; R$^2$ is hydrogen, hydroxy, C$_{1-5}$ alkyl or —CH$_2$CH$_2$C(=O)NH$_2$; R$^3$ and R$^4$ are independently hydrogen, C$_{1-7}$ alkyl, —C(=X)—R$^5$, or 2-, 3- or 4-pyridyl, prymidyl or phenyl substituted with one or two selected from a group consisting of halogen, C$_{1-6}$ alkoxy, nitro, trifluoromethyl, C$_{1-6}$ alkyl and carboxyl, or R$^3$ and R$^4$ are directly bonded by C$_{3-4}$ containing oxygen, sulfur or nitrogen to form a heterocyclic ring, X is oxygen, sulfur or NH and R$^5$ is C$_{1-7}$ alkyl, —NHR$^6$, CONH$_2$ or 2-, 3- or 4-pyridyl, prymidyl or phenyl substituted with one selected from a group consisting of halogen, C$_{1-6}$ alkoxy, nitrile, trifluoromethyl, C$_{1-6}$ alkyl and carboxyl, and R$^6$ is hydrogen, hydroxy, NH$_2$, C$_{1-5}$ alkoxy, C$_{1-5}$ alkyl, pyridyl or phenyl.

(I)

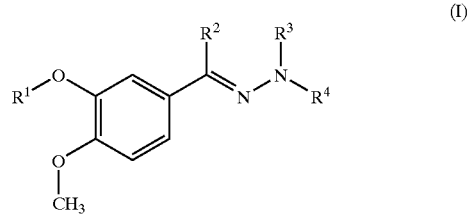

6 Claims, No Drawings

CATHECOL HYDRAZONE DERIVATIVES, PROCESS FOR PREPARING THE SAME AND PHARMACEUTICAL COMPOSITION CONTAINING THE SAME

This application is the national phase under 35 U.S.C. §371 of PCT International Application No. PCT/KR99/00264 which has an International filing date of May 28, 1999, which designated the United States of America and was published in English.

FIELD OF THE INVENTION

The present invention relates to novel cathecol hydrazone derivatives which inhibit the enzymatic activity of phosphodiesterase IV or tumor necrosis factor. These compounds may be useful in prevention or treatment of bronchial asthma, arthritis, bronchitis, chronic atretic airway, psoriasis, allergic rhinitis, dermatitis, AIDS, Crohn's disease, septicemia, septic shock, other inflammatory diseases such as cachexia, TNF related diseases, etc. Also, the present invention relates to a method for producing said compounds and a pharmaceutical composition containing said compound.

BACKGROUND OF THE INVENTION

Phosphodiesterase IV is an enzyme that specifically hydrolyzes cAMP (cyclic adenosine 3',5'-monophosphate) into inactive adenosine 3',5'-monophosphate. The cAMP has been shown to be a second messenger mediating the cellular responses to external stimuli and to act as relaxing or contradicting bronchial muscles.

The inhibition of phosphodiesterase IV leads to the prevention of broncospasm by maintaining the concentration of cAMP and also induces an anti-inflammation. Therefore, compounds that inhibit phosphodiesterase IV should be effective in treating asthma and the like diseases.

It is known that tumor necrosis factor (TNF) is implicated in infectious disease such as cachexia and autoimmune disease. Also, TNF appears to act as a primary mediator for inflammatory reaction such as septicemia and septic shock.

Therefore, it is expected that compounds with the inhibitory activity against phosphodiesterase IV or TNF will be pharmaceutically valuable and there is always a need to develop new compounds which inhibit phosphodiesterase IV and TNF.

Many compounds have been suggested as inhibitors of phosphodiesterase IV and TNF. For example, EP 470,805 of American Home Product describes oximcarbamate and oximcarbonate of formula:

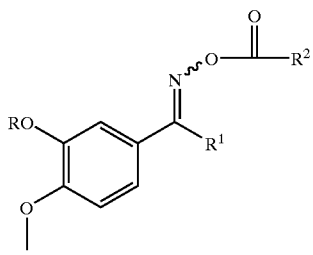

wherein R is $C_{3-7}$ alkyl or $C_{3-7}$ cycloalkyl, $R^1$ is halogen or lower alkyl, and $R^2$ is amino, lower alkylamino, arylamino, lower alkoxy or aryloxy.

U.S. Pat. No. 5,393,798 of SmithKline Beecham Corporation describes phenylalkyl oxamide compound of formula:

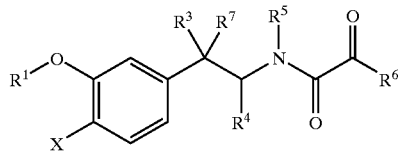

wherein $R^1$ is $C_{4-6}$ cycloalkyl, X is $YR^2$ halogen in which Y is oxgen or sulfur, or lower alkyl, $R^3$ and $R^5$ are independently $OR^7$, $R^4$ is hydrogen or $C_{1-2}$ alkyl, $R^6$ is $OR_7$ or $NR_7OR_7$, and $R^7$ is hydrogen or $C_{1-3}$ alkyl.

SUMMARY OF THE INVENTION

The present invention provides novel cathecol hydrazone derivatives of formula I:

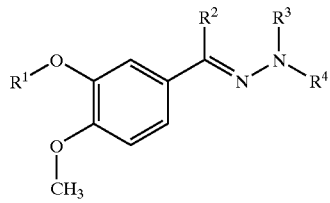

or pharmaceutically acceptable salts thereof, wherein $R^1$ is $C_{1-7}$ alkyl or $C_{3-7}$ cycloalkyl;

$R^2$ is hydrogen, hydroxy, $C_{1-5}$ alkyl or —$CH_2CH_2C(=O)NH_2$;

$R^3$ and $R^4$ are independently hydrogen, $C_{1-7}$ alkyl, —C(=X)—$R^5$, or 2-, 3- or 4-pyridyl, prymidyl or phenyl substituted with one or two selected from a group consisting of halogen, $C_{1-6}$ alkoxy, nitro, trifluoromethyl, $C_{1-6}$ alkyl and carboxyl, or $R^3$ and $R^4$ are directly bonded by $C_{3-4}$ containing oxygen, sulfur or nitrogen to form a heterocyclic ring, X is oxygen, sulfur or NH, and $R^5$ is $C_{1-7}$ alkyl, —$NHR^6$, $CONH_2$ or 2-, 3- or 4-pyridyl, prymidyl or phenyl substituted with one selected from a group consisting of halogen, $C_{1-6}$ alkoxy, nitrile, trifluoromethyl, $C_{1-6}$ alkyl and carboxyl, and $R^6$ is hydrogen, hydroxy, $NH_2$, $C_{1-5}$ alkoxy, $C_{1-5}$ alkyl, pyridyl or phenyl.

DETAILED DESCRIPTION OF THE INVENTION

The compound of formula I can be present as optical isomers or stereoisomers. Thus, the present invention includes such isomers and mixtures thereof.

The present invention provides a pharmaceutical composition for inhibiting phosphodiesterase IV or TNT which comprises a compound of formula I and a pharmaceutically acceptable carrier.

The compound of formula I can be prepared by the following reaction scheme I:

Reaction Scheme I

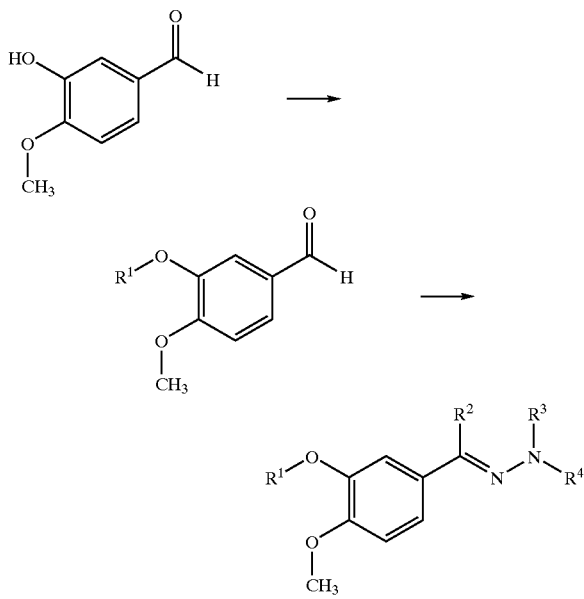

wherein R¹, R², R³ and R⁴ are the same as defined above.

Some derivatives were synthesized by a known method (J. Med. Chem., 1994, 37, 1696). Hydrazine compounds were synthesized in yield of 60% to 90% in alcohol solvent using acid catalyst (Tetrahedron Lett. 1994, 35, 3711).

The invention will now be described with reference to the following illustrative Examples.

EXAMPLES

Reference Example 1

3-cyclopentyloxy-4-methoxybenzaldehyde

A solution of 100 g (0.66 mol) of isovanillin, 136.2 g (0.99 mol) of anhydrous potassium carbonate, and 3 g of potassium iodide in 650 ml of anhydrous dimethylformamide was stirred at 65° C. 127.3 g (0.85 mol) of cyclopentyl bromide was slowly added dropwise for 1 hour to the solution. This solution was stirred at 65° C. for 1 day and, then, its temperature was lowered to a room temperature. It was diluted by 2.0 L of toluene and was washed with 1M sodium hydroxide (2×1.5 L). The aqueous layer was extracted with 0.5 L of toluene, and the organic layer was washed with distilled water (2×1.5 L). The organic layer was dried and concentrated to obtain 117 g of light brown oily title compound. $^1$H NMR(CDCl$_3$,d): 9.84(s, 1H) 7.42(m, 2H) 6.95(d, 1H, J=9 Hz) 4.87(m, 1H) 3.93(s, 3H) 2.1–6(m, 8H)

Example 1

(E)-3-cyclopentyloxy-4-methoxybenzaldehyde isonicotinic hydrazone

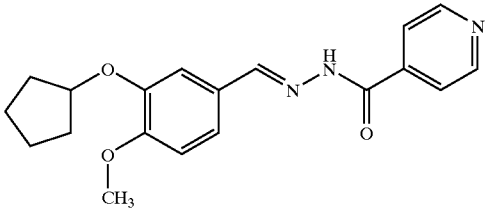

A catalytic amount of concentrated sulfuric acid was added to a solution of 0.44 g (2.0 mmole) of compound prepared by Reference Example 1 in 30 ml of ethanol and the mixture was stirred at room temperature for 10 minutes. 0.33 g of isonicotinic hydrazide was added to the reaction solution. The solution was stirred at 50° C. for 4 hours and was concentrated under reduced pressure. The residue was dissolved in dichloromethane and was washed twice with 50 ml of distilled water. The separated organic layer was dried over anhydrous magnesium sulfate and was distilled under reduced pressure. The resulting white crystal was recrystallized in dichloromethane to obtain 0.67 g (88.45%) of white title compound. m.p. 170–171° C. $^1$H NMR(DMSO-d6): 1.60(2H, m) 1.75(4H, m) 1.92(2H, m) 3.81(3H, s) 4.85(1H, m) 7.04(1H, d J=8.4 Hz) 7.24(1H, dd, J=8.4, 1.8 Hz) 7.33(1H, d J=1.8 Hz) 7.81(2H, dd J=4.5, 1.6 Hz) 8.39(1H, s) 8.78(2H, dd, J=4.5, 1.6 Hz) 11.92(1H, s)

Example 2

(E)-ethyl[(3-cyclopentyloxy-4-methoxyphenyl) methylene]hydrazinoformate

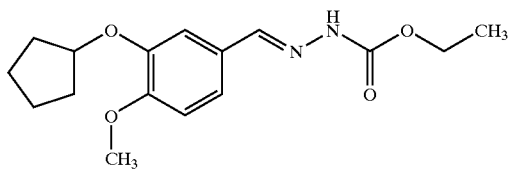

A catalytic amount of concentrated hydrochloric acid was added to a solution of 1.00 g (4.54 mmole) of compound prepared by Reference Example 1 in 80 ml of ethanol and the mixture was stirred at room temperature for 10 minutes. 0.73 g of ethyl carbazate was added to the reaction solution. The solution was stirred at 50° C. for 4 hours and was concentrated under reduced pressure. The residue was dissolved in dichloromethane and was washed twice with 50 ml of distilled water. The separated organic layer was dried over anhydrous magnesium sulfate and was distilled under reduced pressure. The resulting white crystal was recrystallized in dichloromethane to obtain 1.25 g (89.87%) of white title compound. m.p. 146–147° C. $^1$H NMR(DMSO-d6): 1.23(3H, t, J=7.1 Hz) 1.58(2H, m) 1.73(4H, m) 1.88(2H, m) 3.77(3H, s) 4.13(2H, q, J=7.1 Hz) 4.80(1H, m) 6.98(1H, d J=8.4 Hz) 7.07(1H, dd, J=8.4, 1.9 Hz) 7.20(1H, d J=1.9 Hz) 7.93(1H, s) 10.92(1H, s)

Example 3

(E)-3-cyclopentyloxy-4-methoxybenzaldehyde phenylhydrazone

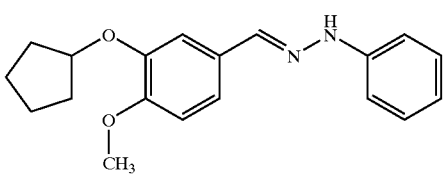

A catalytic amount of concentrated hydrochloric acid was added to a solution of 0.50 g (2.27 mmole) of compound prepared by Reference Example 1 in 60 ml of ethanol and the mixture was stirred at room temperature for 10 minutes. 0.34 ml of phenylhydrazine was added to the reaction solution. The solution was stirred at 50° C. for 10 hours. The resulting precipitate was filtered and washed with 20 ml of ethanol to obtain 0.63 g (89.41%) of white title compound. m.p. 138–140° C. $^1$H NMR(DMSO-d6): 1.60(2H, m) 1.75(4H, m) 1.92(2H, m) 3.77(3H, s) 4.85(1H, m) 6.72(1H, m) 6.95(1H, d J=8.2 Hz) 7.03(2H, d, J=7.6 Hz) 7.09(1H, dd, J=8.2, 1.8 Hz) 7.20(2H,t) 7.26(1H, d J=1.8 Hz) 7.78(1H, s) 10.12(1H, s)

Example 4

(E)-3-cyclopentyloxy-4-methoxybenzaldehyde acetic hydrazone

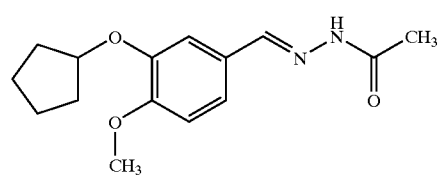

A catalytic amount of concentrated hydrochloric acid was added to a solution of 0.50 g (2.27 mmole) of compound prepared by Reference Example 1 in 60 ml of ethanol and the mixture was stirred at room temperature for 10 minutes. 0.26 g of acetic hydrazide was added to the reaction solution. The solution was stirred at 25° C. for 10 hours and was concentrated under reduced pressure. The residue was dissolved in dichloromethane and was washed twice with 50 ml of distilled water. The separated organic layer was dried over anhydrous magnesium sulfate and was distilled under reduced pressure. The resulting white crystal was recrystallized in dichloromethane to obtain 0.59 g (94.06%) of white title compound. m.p. 155–156° C. $^1$H NMR(DMSO-d6): 1.58(2H, m) 1.71(4H, m) 1.88(2H, m) 2.18(3H, s) 3.78(3H, s) 4.81(1H, m) 6.99(1H, d J=8.4 Hz) 7.14(1H, dd, J=8.4, 1.8 Hz) 7.24(1H, d J=1.8 Hz) 7.88(1H, s) 11.12(1H, s)

Example 5

(E)-3-cyclopentyloxy-4-methoxybenzaldehyde 7-chloroquinolone-4-ylhydrazone

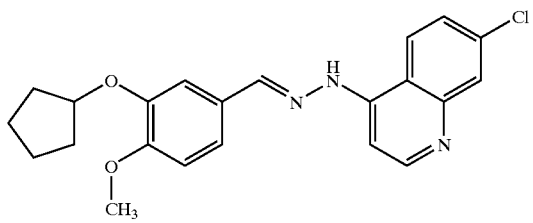

A catalytic amount of concentrated hydrochloric acid was added to a solution of 0.50 g (2.27 mmole) of compound prepared by Reference Example 1 in 60 ml of ethanol and the mixture was stirred at room temperature for 10 minutes. 0.67 g of 7-chloro-4-hydrazinoquinoline was added to the reaction solution. The solution was stirred at 45° C. for 10 hours. The resulting precipitate was filtered and washed with 20 ml of ethanol to obtain 0.55 g (61.20%) of white title compound. m.p. 210–212° C. $^1$H NMR(DMSO-d6): 1.61(2H, m) 1.78(4H, m) 1.94(2H, m) 3.81(3H, s) 4.89(1H, m) 7.04(1H, d J=8.3 Hz) 7.28(1H, dd, J=8.3, 1.8 Hz) 7.36(1H, d J=5.2 Hz) 7.42(1H, d J=1.8 Hz) 7.61(1H, d) 7.86(1H, s) 8.39(1H, s) 8.44(2H, d J=9.1 Hz)

Example 6

(E)-3-cyclopentyloxy-4-methoxybenzaldehyde 2-imidazolinohydrazone

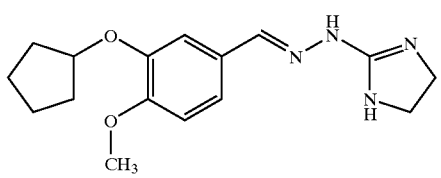

A catalytic amount of concentrated hydrochloric acid was added to a solution of 0.50 g (2.27 mmole) of compound prepared by Reference Example 1 in 50 ml of ethanol and the mixture was stirred at room temperature for 10 minutes. 0.63 g of hydrozino-2-imidazoline hydrobromide was added to the reaction solution. The solution was stirred at 45° C. for 8 hours and was concentrated under reduced pressure. The residue was dissolved in dichloromethane and was washed twice with 50 ml of distilled water. The separated organic layer was dried over anhydrous magnesium sulfate and was distilled under reduced pressure. The resulting light yellow oil was purified by a flash chromatography (silica gel, 7.5% methanol-dichloromethane as a developing solution) to obtain 0.45 g (65.56%) of white title compound. m.p. 87–90° C. $^1$H NMR(DMSO-d6): 1.61(2H, m) 1.72(4H, m) 1.89(2H, m) 3.70(4H, s) 3.79(3H, s) 4.89(1H, m) 7.01(1H, d J=8.4 Hz) 7.24(1H, dd, J=8.4, 1.8 Hz) 7.44(1H, d J=1.8 Hz) 8.06(1H, s)

Example 7

(E)-2-[(3-cyclopentyloxy-4-methoxyphenyl)methylene]hydrazinecarboxamide

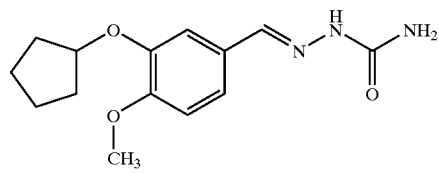

A reaction as in Example 6 was carried out using 0.50 g (2.27 mmole) of compound prepared in Reference Example 1 as a starting material to obtain 0.47 g (74.66%) of white title compound. m.p. 144–146° C. $^1$H NMR(DMSO-d6): 1.58(2H, m) 1.71(4H, m) 1.89(2H, m) 3.76(3H, s) 4.92(1H, m) 6.44(2H, brs) 6.93(1H, d J=8.3 Hz) 7.09(1H, dd, J=8.3, 1.9 Hz) 7.36(1H, d J=1.9 Hz) 7.75(1H, s) 10.08(1H, s)

Example 8

(E)-3-cyclopentyloxy-4-methoxybenzaldehyde 2-nitrophenylhydrazone

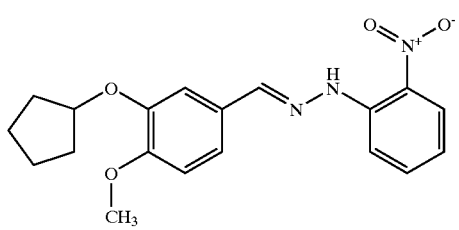

A reaction as in Example 3 was carried out using 0.50 g (2.27 mmole) of compound prepared in Reference Example 1 as a starting material to obtain 0.63 g (78.09%) of red yellow title compound. m.p. 135° C. (decomposed) $^1$H NMR(DMSO-d6): 1.61(2H, m) 1.77(4H, m) 1.94(2H, m) 3.80(3H, s) 4.88(1H, m) 6.89(1H, m) 7.03(1H, d J=8.4 Hz) 7.22(1H, dd, J=8.4, 1.9 Hz) 7.35(1H, d J=1.9 Hz) 7.66(1H, t J=1.6 Hz) 7.95(1H, d J=8.7 Hz) 8.11(1H, dd J=8.5, 1.4 Hz) 8.39(1H, s) 11.15(1H, s)

Example 9

(E)-2-[(3-cyclopentyloxy-4-methoxyphenyl)methylene]hydrazinecarbothioamide

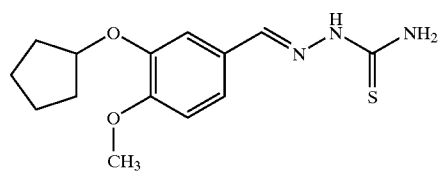

A reaction as in Example 6 was carried out using 1.00 g (4.54 mmole) of compound prepared in Reference Example 1 as a strating material to obtain 0.94 g (70.57%) of white title compound. m.p. 112–114° C. 1H NMR(DMSO-d6): 1.57(2H, m) 1.71(4H, m) 1.88(2H, m) 3.76(3H, s) 4.91(1H, m) 6.44(2H, brs) 6.93(1H, d J=8.4 Hz) 7.09(1H, dd, J=8.4, 1.9 Hz) 7.36(1H, d J=1.9 Hz) 7.74(1H, s) 10.06(1H, s)

Example 10

(E)-3-cyclopentyloxy-4-methoxybenzaldehyde 4chlorophenylhydrazone

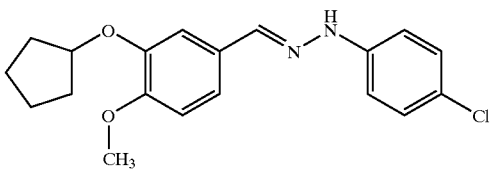

A reaction as in Example 6 was carried out using 1.50 g (6.81 mmole) of compound prepared in Reference Example 1 as a starting material to obtain 1.65 g (70.26%) of white title compound. m.p. 133–135° C. $^1$H NMR(DMSO-d6): 1.60(2H, m) 1.76(4H, m) 1.91(2H, m) 3.78(3H, s) 4.86(1H, m) 6.97(1H, d J=8.4 Hz) 7.04(2H, dd J=6.8, 2.1 Hz) 7.12(1 H, dd, J=8.4, 1.9 Hz) 7.24(2H, dd J=6.8, 2.1 Hz) 7.27(1H, d J=1.9 Hz) 7.87(1H, s) 10.27(1H, s)

Example 11

(E)-2[(3-cyclopentyloxy-4-methoxyphenyl)methylene]hydrazinecarbonylmethyl(trimethyl)ammonium chloride

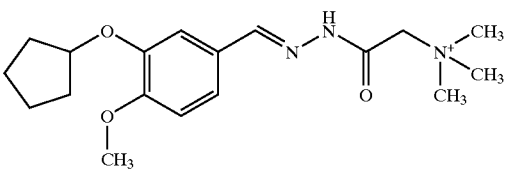

A reaction as in Example 6 was carried out using 1.50 g (6.81 mmole) of compound prepared in Reference Example 1 and 1.03 g of (carboxymethyl)trimethylammonium chloride hydrazide as starting materials to obtain 1.73 g (68.68%) of white title compound. m.p. 178–179° C. $^1$H NMR(DMSO-d6): 1.60(2H, m) 1.73(4H, m) 1.90(2H, m) 3.30(9H, s) 3.79(3H, s) 4.33(2Ha, s) 4.79(2Ha, s) 4.84(1H, m) 7.03(1H, d J=8.4 Hz) 7.23(1H, dd, J=8.4, 1.8 Hz) 7.29(1H, d J=1.8 Hz) 8.01(1Ha',s) 8.26(1Ha', s) 12.05(1H, brs)

Example 12

(E)-N-(1,4-oxazine-4-yl)-3-cyclopentyloxy-4-methoxyphenylmethaneimine

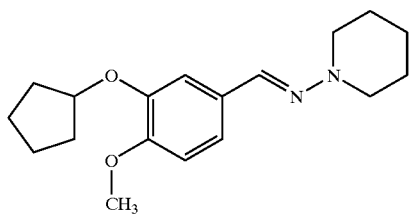

5.0 g (22.7 mmole) of compound prepared by Reference Example 1 was dissolved in 60 ml of ethanol and the resulting solution was stirred at room temperature for 10 minutes. 2.91 ml of N-aminomorpholine was added to the reaction solution. The solution was stirred at 5° C. for 14 hours. The resulting precipitate was filtered and washed with 20 ml of ethanol to obtain a while solid. This solid was recrystallized in isopropylether to obtain 6.37 g (92.19%) of title compound. m.p. 108–109° C. ¹H NMR(DMSO-d6): 1.56(m, 2H) 1.70(m, 4H) 1.88(m, 2H) 3.03(m, 4H) 3.67(m, 7H) 4.77(m, 1H) 6.88(d, 1H) 7.04(dd, 1H) 7.18(d, 1H) 7.62(s, 1H)

Example 13

(E)-N-piperidino-3-cyclopentyloxy-4-methoxyphenylmethaneimine

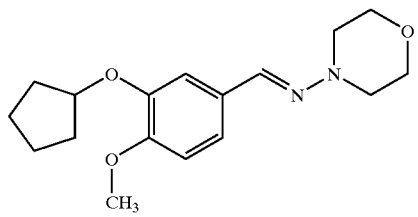

A reaction as in Example 12 was carried out using 0.50 g (2.27 mmole) of compound prepared in Reference Example 1 and 0.31 ml of N-aminopiperidine as starting materials to obtain 0.65 g (94.68%) of white title compound. m.p. 81–82° C. ¹H NMR(DMSO-d6): 1.52(m, 4H) 1.67(m, 8H) 1.90(m, 2H) 3.04(m, 4H) 3.70(s, 3H) 4.76(m, 1H) 6.89(d, 1H) 7.04(dd, 1H) 7.i8(d, 1H) 7.57(s, 1H)

Example 14

(E)-2-[(3-cyclopentyloxy-4-methoxyphenyl)methylene]hydrazinecarboximidamide

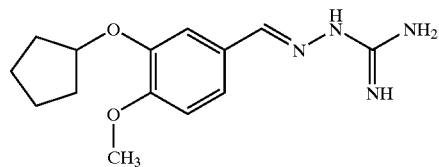

A reaction as in Example 6 was carried out using 1.50 g (6.81 mmole) of compound prepared in Reference Example 1 and 0.73 g of aminoguanidine hydrochloride as starting materials to obtain 1.60 g (85.02%) of white title compound. m.p. 100–103° C. ¹H NMR(DMSO-d6): 1.62~1.64(2H, m) 1.74~1.78(4H, m) 1.94~1.97(2H, m) 3.84(3H, s) 4.95~4.98 (1H, m) 7.05(1H, d J=8.4 Hz) 7.33(1H, dd, J=8.4, 2.0 Hz) 7.54(1H, d J=1.9 Hz) 7.7(1H, brs) 8.36(1H, s) 11.69(1H, s)

Example 15

(E)-3-cyclopentyloxy-4-methoxybenzaldehyde 2-pyridinylhydrazone

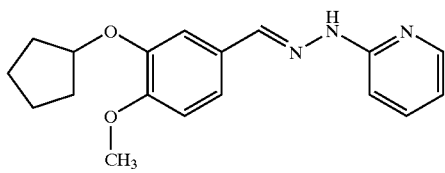

A reaction as in Example 6 was carried out using 0.80 g (3.63 mmole) of compound prepared in Reference Example 1 and 0.39 g of 2-hydrazinopyrimidine as starting materials to obtain 0.96 g (84.89%) of white title compound. m.p. 142–143 ° C. ¹H NMR(DMSO-d6): 1.58~1.61 (2H, m) 1.71 ~1.76(4H, m) 1.89~1.94(2H, m) 3.77(3H, s) 4.84~4.87(1H, m) 6.73~6.74(1H, m) 6.97(1H, d J=8.3 Hz) 7.10(1H, dd, J=8.3, 1.8 Hz) 7.20(1H, d J=8.4 Hz)7.27(1H, d J=1.8 Hz) 7.62~7.63(1H, m) 7.94(1H, s) 8.09(1H, dd J=4.9, 1.0 Hz) 10.67(1H, s)

Example 16

(E)-3-cyclopentyloxy-4-methoxybenzaldehyde 2-carboxyphenylhydrazone

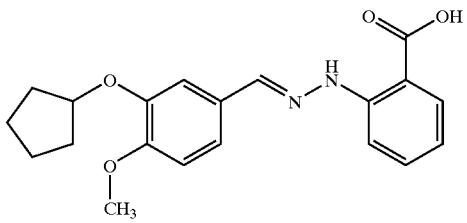

A reaction as in Example 6 was carried out using 0.80 g (3.63 mmole) of compound prepared in Reference Example 1 and 0.66 g of 2-hydrazinobenzoic hydrochloride as starting materials to obtain 1.05 g (81.57%) of white title compound. m.p. 174–176° C. ¹H NMR(DMSO-d6): 1.59~1.60(2H, m) 1.71~1.76(4H, m) 1.92~1.93(2H, m) 3.78 (3H, s) 4.85(1H, m) 6.78(1H, dd J=7.0, 1.0 Hz) 6.99(1H, d J=8.4 Hz) 7.20(1H, dd, J=8.4, 1.9 Hz) 7.32(1H, d J=1.9 Hz) 7.50(1H, dd J=7.0, 1.6 Hz) 7.68(1H, dd J=8.5, 0.8 Hz) 7.84(1H, dd J=8.0, 1.4 Hz) 8.05(1H, s) 8.79(1H, d J=4.9 Hz) 11.17(1H, s)

Example 17

(E)-3-cyclopentyloxy-4-methoxybenzaldehyde 4-trifluoromethylpyrimidin-2-ylhydrazone

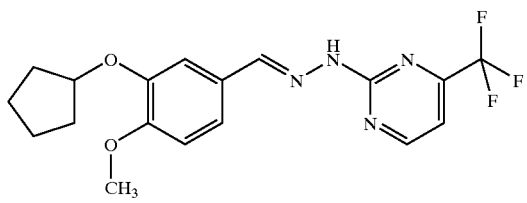

A reaction as in Example 6 was carried out using 0.80 g (3.63 mmole) of compound prepared in Reference Example 1 and 0.63 g of 2-hydrazino-4-(trifluoromethyl)pyrimidine as starting materials to obtain 1.10 g (79.62%) of white title compound. m.p. 73–75° C. ¹H NMR(DMSO-d6): 1.58~1.59 (2H, m) 1.72~1.76(4H, m) 1.89(2H, m) 3.79(3H, s) 4.81~4.84(1H, m) 7.01(1H, d J=8.4 Hz) 7.19(1H, dd, J=8.4, 2.0 Hz) 7.21(1H, d J=4.9 Hz) 7.27(1H, d J=2.0 Hz) 8.11(1H, s) 8.79(1H, d J =4.9 Hz) 1.67(1H, s)

Example 18

(E)-2-[(3-cyclopentyloxy-4-methoxyphenyl)methylene]hydrazinecarbohydrazine

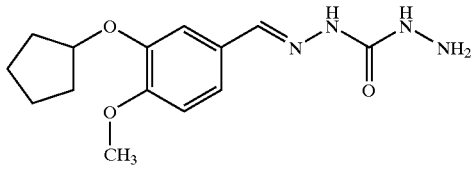

A catalytic amount of glacial acetic acid was added to a solution of 1.0 g (4.54 mmol) of compound prepared in Reference Example 1 in 50 ml of methanol and the mixture was stirred at room temperature for 10 minutes and added dropwise over 20 minutes to a solution of 1.0 g of carbohydrazine in 50 ml of distilled water. The reaction mixture was stirred at room temperature for 1 hour and the precipitated solids were filtered to obtain 0.89 g (67.06%) of white title compound. m.p. 179–181° C. $^1$H NMR(DMSO-$d_6$): 1.61(2H, m) 1.72(4H, m) 1.89(2H, m) 3.76(3H, s) 4.05(2H, brs) 4.94(1 H,m) 6.92(1H, d J=8.3 Hz) 7.07(1H, dd, J=8.3, 1.7 Hz) 7.42(1H, d J=1.6 Hz) 7.74(1H, s) 8.03(1H,s) 10.23 (1H,s)

Example 19

(E)-2-[(3-cyclopentyloxy-4-methoxyphenyl)methylene]hydrazinedicarboxamide

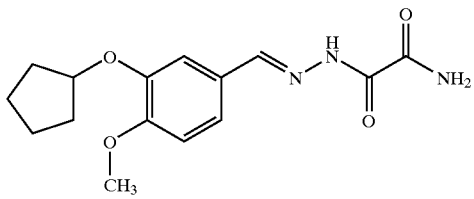

A catalytic amount of glacial acetic acid was added to a solution of 1.0 g (4.54 mmol) of compound prepared in Reference Example 1 in 50 ml of methanol and the mixture was stirred at room temperature for 10 minutes and added dropwise over 30 minutes to a solution of 1.17 g of oxamic hydrazide in 60 ml of distilled water. The reaction mixture was stirred at room temperature for 2 hours and the precipitated solids were filtered to obtain 1.12 g (80.80%) of white title compound. m.p. 233–235° C. $^1$H NMR(DMSO-$d_6$): 1.57(2H, m) 1.71(4H, m) 1.87(2H, m) 3.76(3H, s) 4.11(2H, brs) 4.95(1H,m) 6.91(1H, d J=8.5 Hz) 7.28(1H, dd, J=8.5, 2.2 Hz) 7.42(1H, d J=2.1 Hz) 7.83(1H, s) 9.32(1H,s)

Example 20

(E)-2-[(3-cyclopentyloxy-4-methoxyphenyl)methylene]hydrazinoacetic acid

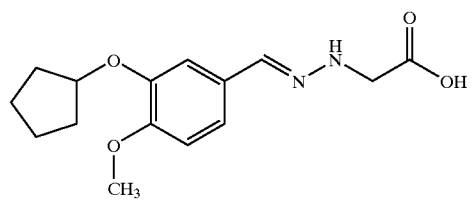

A reaction as in Example 6 was carried out using 0.80 g (3.63 mmole) of compound prepared in Reference Example 1 and 0.63 g of ethylhydrazinoacetate as starting materials to obtain 0.98 g of white ethyl (E)-2-[3-cyclopentyloxy-4-methoxyphenylmethylene]hydrazinoacetate. The prepared ester compound was hydrolysed in the mixture of methanol and 1.0 N aqueous sodium hydroxide solution to afford 0.75 g (70.77%) of white title solid. m.p. 165° C. (decomposed) $^1$H NMR(DMSO-$d_6$): 1.59(2H, m) 1.71(4H, m) 1.87(2H, m) 3.74(3H, s) 3.83(2H, brs) 4.77(1H,m) 6.90(1H, d J=8.5 Hz) 6.96(1H, dd, J=8.3, 1.7 Hz) 7.09(1H, d J=1.7 Hz) 7.57(1H, s)

Experimental Example

Inhibition of Phosphodiesterase IV Activity

Compounds prepared by Examples 1 through 16 and Rolipram as control were tested on the inhibition of phosphodiesterase IV.

Phosphodiesterase IV partially purified from human U937 cells, test compound and 1.0 uM cAMP including 0.01 uM[$^3$H]cAMP were incubated at 30° C. for 20 minutes. The PDE reaction to convert cAMP into AMP was completed by boiling the reaction solution for 2 minutes. AMP was converted into adenosine by adding snake venom nucleotidase and incubating the reaction solution at 30° C. for 10 minutes. While unhydrolyzed cAMPs were bonded to AG1-X2 resin, the [$^3$H]adenosine in the aqueous solution was quantified by scintillation counting. The results are shown in Table I below, in which the values indicate inhibition (%) of the PDE IV by each test compound.

TABLE I

| Test Compounds | Concentration (uM) | Inhibition (%) |
|---|---|---|
| Rolipram (Control) | 20 | 70.1 |
|  | 2 | 62.5 |
| EXAMPLE 1 | 20 | 66.7 |
|  | 2 | 38.4 |
| EXAMPLE 2 | 20 | 63.7 |
|  | 2 | 46.7 |
| EXAMPLE 3 | 20 | 80.4 |
|  | 2 | 46.6 |
| EXAMPLE 4 | 20 | 72.1 |
|  | 2 | 51.7 |
| EXAMPLE 5 | 20 | 64.9 |
|  | 2 | 37.9 |
| EXAMPLE 6 | 20 | 58.3 |
|  | 2 | 31.7 |
| EXAMPLE 7 | 20 | 89.7 |
|  | 2 | 66.2 |
| EXAMPLE 9 | 20 | 81.0 |
|  | 2 | 69.0 |
| EXAMPLE 10 | 20 | 70.7 |
|  | 2 | 39.3 |
| EXAMPLE 11 | 20 | 45.1 |
|  | 2 | 43.3 |
| EXAMPLE 12 | 20 | 79.4 |
|  | 2 | 62.9 |
| EXAMPLE 13 | 20 | 73.3 |
|  | 2 | 31.4 |
| EXAMPLE 14 | 20 | 57.7 |
|  | 2 | 14.7 |
| EXAMPLE 15 | 20 | 63.6 |
|  | 2 | 49.4 |
| EXAMPLE 16 | 20 | 76.6 |
|  | 2 | 42.3 |

What is claimed is:

1. A method of treating a disorder responsive to inhibition of phosphodiesterase IV or tumor necrosis factor (TNF), comprising administering to a patient in need of such treatment an effective amount of a compound of the formula:

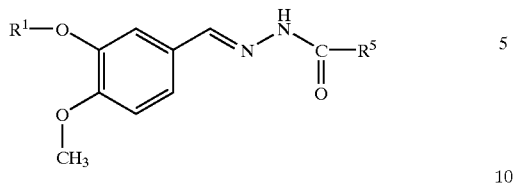

or pharmaceutically acceptable salts thereof, wherein
$R^1$ is $C_{3-7}$ cycloalkyl; and
$R^5$ is $C_{1-7}$alkyl, —$NH_2$, —$NHNH_2$, —$CONH_2$, 4-pyridyl, $C_{1-6}$alkoxy, or trimethylaminomethyl.

2. The method according to claim 1 wherein the compound is $R^5$ 2-[(3-cyclopentyloxy-4-methoxyphenyl)methylene]hydrazine carboxamide.

3. The method according to claim 1 wherein the compound is selected from the group consisting of:

(E)-3-cyclopentyloxy-4-methoxybenzaldehyde isonicotinic hydrazone,
(E)-ethyl[(3-cyclopentyloxy-4-methoxyphenyl)methylene] hydrazinoformate,
(E)-3-cyclopentyloxy-4-methoxybenzaldehyde acetic hydrazone,
(E)-2-[(3-cyclopentyloxy-4-methoxyphenyl)methylene] hydrazine carboxamide,
(E)-2-[(3-cyclopentyloxy-4-methoxyphenyl)methylene] hydrazine carbonylmethyl(trimethyl)ammonium chloride,
(E)-2-[(3-cyclopentyloxy-4-methoxyphenyl)methylene] hydrazine carbohydrazine, and
(E)-2-[(3-cyclopentyloxy-4-methoxyphenyl)methylene] hydrazine dicarboxamide.

4. A process for preparing a compound of formula I:

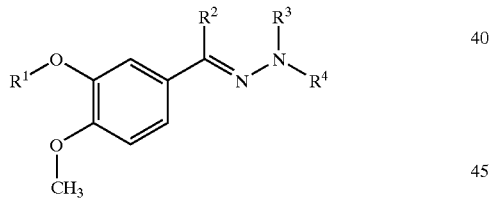

or pharmaceutically acceptable salt, wherein
$R^1$ is $C_{3-7}$ cycloalkyl;
$R^2$ is hydrogen;
$R^3$ is hydrogen;
$R^4$ is —C(=X)—$R^5$;
X is oxygen;
$R^5$ is $C_{1-7}$alkyl, —$NHR_6$, —$CONH_2$, 4-pyridyl, $C_{1-6}$alkoxy, or trimethylaminomethyl, and
$R^6$ is hydrogen or —$NH_2$ which comprises reacting $C_{3-7}$ cycloalkyl with a compound of formula II:

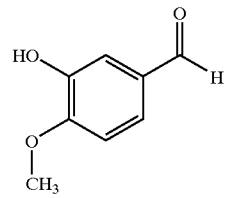

to produce a compound of formula III:

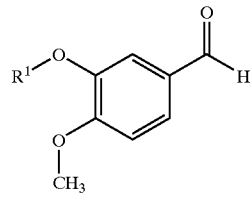

wherein $R^1$ is the same as defined above, and reacting the compound of formula III with a compound of formula IV:

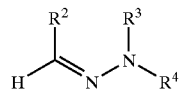

wherein $R^2$, $R^3$ and $R^4$ are the same as defined above.

5. A pharmaceutical composition for inhibiting phosphodiesterase IV or TNF which comprises: a pharmaceutically effective amount of the compound of the formula

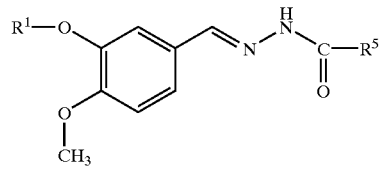

or pharmaceutically acceptable salts thereof, wherein $R^1$ is $C_{3-7}$ cycloalkyl; $R^5$ is $C_{1-7}$alkyl, —$NH_2$, —$NHNH_2$, —$CONH_2$, 4-pyridyl, $C_{1-6}$alkoxy, or trimethylaminomethyl; and a pharmaceutically acceptable carrier.

6. The method of claim 1, wherein the disorder responsive to inhibition of phosphodiesterase IV is asthma and wherein the disorder responsive to TNF is septicemia and septic shock.

* * * * *